(12) United States Patent
Zhang et al.

(10) Patent No.: US 7,555,098 B2
(45) Date of Patent: Jun. 30, 2009

(54) METHOD AND APPARATUS FOR X-RAY FLUORESCENCE ANALYSIS AND DETECTION

(75) Inventors: Ke Zhang, Bolingbrook, IL (US); Gerold Rosenbaum, Lemont, IL (US)

(73) Assignee: HD Technologies Inc., Burr Ridge, IL (US)

( * ) Notice: Subject to any disclaimer, the term of this patent is extended or adjusted under 35 U.S.C. 154(b) by 0 days.

(21) Appl. No.: 11/768,096

(22) Filed: Jun. 25, 2007

(65) Prior Publication Data
US 2008/0273663 A1 Nov. 6, 2008

Related U.S. Application Data

(60) Provisional application No. 60/915,595, filed on May 2, 2007.

(51) Int. Cl.
*G21K 1/06* (2006.01)
(52) U.S. Cl. .......................... 378/85; 378/84
(58) Field of Classification Search .......... 378/84, 378/85
See application file for complete search history.

(56) References Cited

U.S. PATENT DOCUMENTS

| | | | | | |
|---|---|---|---|---|---|
| 5,173,930 | A | * | 12/1992 | Hoover | 378/85 |
| 5,192,869 | A | * | 3/1993 | Kumakhov | 250/505.1 |
| 5,646,976 | A | * | 7/1997 | Gutman | 378/84 |
| 5,745,543 | A | * | 4/1998 | De Bokx et al. | 378/45 |
| 5,799,056 | A | | 8/1998 | Gutman | |
| 6,317,483 | B1 | * | 11/2001 | Chen | 378/84 |
| 6,421,417 | B1 | * | 7/2002 | Jiang et al. | 378/84 |
| 6,628,748 | B2 | * | 9/2003 | Michaelsen et al. | 378/44 |
| 6,823,042 | B2 | * | 11/2004 | Hayashi et al. | 378/84 |
| 7,242,746 | B2 | * | 7/2007 | Michaelsen et al. | 378/84 |

OTHER PUBLICATIONS

Zhang, "A High Resolutions X-ray Fluorescence Detector," Database: CRISP, NIH Grant No. 2R44RR015994-02 (2003) (Abstract).
Zhang, "A High Resolutions X-ray Fluorescence Detector," Database: CRISP, NIH Grant No. 5R4RR015994-03 (2004) (Abstract).
Zhang, "Biocat Multilayer Analyzer," Database: CRISP, NIH Grant No. 5U41RR008630-040002 (1998) (Abstract).
Zhang, "Biocat Multilayer Analyzer," Database: CRISP, NIH Grant No. 3U41RR008630-04S10002 (1999) (Abstract).

(Continued)

*Primary Examiner*—Allen C. Ho
(74) *Attorney, Agent, or Firm*—Barnes & Thornburg LLP; Alice O. Martin

(57) ABSTRACT

A detector apparatus is disclosed that includes a housing and a multilayer disposed within the housing. The multilayer defining a leading edge and a trailing edge and is adapted to interact with a plurality of high-energy photons, impingent from the leading edge, to permit passage of photons of at least one selected energy. The multilayer is secured to a first securement adjacent to the leading edge. The multilayer is secured to a second securement bracket adjacent to the trailing edge. At least one detector is disposed adjacent to the trailing edge of the multilayer to detect the impingent high-energy photons. An adjustment mechanism operatively connects to the second securement bracket to adjust the position of the second securement bracket, thereby altering an angular position of the multilayer.

22 Claims, 9 Drawing Sheets

OTHER PUBLICATIONS

Zhang et al., "Energy-Resolving X-ray Fluorescence Detection Using Synthetic Multilayers," *J. Synchrotron Rad.*, 5: 1227-1234 (1998).

Zhang, "High Efficiency X-ray Fluorescence Detectors," Database: CRISP, NIH Grant No. 1R43RR020240-01A1 (2005) (Abstract).

Zhang, "High Resolution X-ray Fluorescence Detector," Database: CRISP, NIH Grant No. 1R43RR015994-01 (2001) (Abstract).

Zhang, "Multilayer Analyser for XAFS: X Ray Fluorescence Detector," Database: CRISP, NIH Grant No. 5U41RR008630-050014 (1999) (Abstract).

Zhang, "Multilayer Analyser for XAFS: X Ray Fluorescence Detector," Database: CRISP, NIH Grant No. 3U41RR008630-05S10014 (2000) (Abstract).

Zhang, "Time Resolved XAFS & Optical Monitoring," Database: CRISP, NIH Grant No. 5U41RR008630-050015 (1999) (Abstract).

Zhang, "Time Resolved XAFS & Optical Monitoring," Database: CRISP, NIH Grant No. 3U41RR008630-05S10015 (2000) (Abstract).

K. Zhang, G. Rosenbaum, R. Liu, C. Liu C. Carmeli, G. Bunker, and D. Fischer, *Development of Multilayer Analyzer Array Detectors for X-ray Fluorescence at the Third Generation Synchrotron Source*, in the American Institute of Physics series of conference proceedings, Eighth International Conference on Synchrotron Radiation Instrumentation, (edit. T. Warwick et al.) pp. 957-960 (2004).

* cited by examiner

METHOD AND APPARATUS FOR X-RAY FLUORESCENCE ANALYSIS AND DETECTION

CROSS-REFERENCE TO RELATED APPLICATIONS

This patent application claims benefit under 35 U.S.C. § 119 of U.S. Provisional Patent Application No. 60/915,595, filed May 2, 2007.

This invention was made with government support under grant No. R44 RR020240 awarded by the National Institutes of Health (NIH). The government has certain rights in the invention.

BACKGROUND

Apparatuses and systems used for spectroscopic analysis are described; for example, analyzers used for detection of fluorescent X-ray spectra.

X-ray fluorescence detection is a commonly used technique in X-ray absorption spectroscopy applications on dilute systems. As would be appreciated by those skilled in the art, the fluorescence signal from the absorption of spectroscopically interesting atoms forms only a small part of a large background spectrum from various sources including coherent and incoherent scattering of X-ray photons.

Statistical fluctuations in the number of scattered background photons are a principal source of noise and significantly degrade the signal-to-noise ratio in X-ray absorption measurements. Thus, discrimination between the desired X-ray fluorescence and the undesired background is essential for fluorescence detection.

For very dilute systems where the background count rate is 10-1000 or more times greater than the signal count rate, energy-resolving detectors with a reasonable solid angle are more desirable. For example, the 13-element pure germanium detector (manufactured by Canberra Corp., with a corporate headquarters in Meriden, Conn., USA) was designed for this purpose. That detector provides an energy resolution of 200 eV at 6 keV and a high total count rate of approximately $2 \times 10^6$ counts/s.

One difficulty with a pure germanium (Ge) detector lies in dead-time losses originating from its associated pulse-counting electronics. Without certain precautions, it is possible that absorption spectra may be distorted. Moreover, the maximum count rate of the detector itself limits the efficiency of data collection.

Modern synchrotron sources that exist currently generate a spectral flux that often exceeds the detector rate limit for Ge detectors. Since stronger sources are being and have been developed, this problem has become worse and will continue to do so.

An increased photon flux, on the order of $10^{11}$-$10^{14}$ photons/s, provides improved opportunities for X-ray spectroscopy applications in probing dilute systems and rapid reactions. However, in dilute systems, such as those involving trace elements in biological and environmental sciences, an increased photon flux is expected to have little positive effect on spectroscopy data collection. Simply put, the efficiency and sensitivity of existing detectors limits the spectroscopic capability of modern synchrotron sources.

Accordingly, a need has developed for detectors and detector systems that operate, without detector saturation, in high photon flux environments to improve detection and data collection efficiency with a reasonable solid angle.

Development of X-ray fluorescence detectors using a multilayer analyzer array provides improved background discrimination.

The application of the detectors is not limited to X-ray absorption spectroscopy. It can be used in X-ray fluorescence analysis and fluorescence imaging.

One report was that linearly graded multilayers provide reasonable background rejection. However, a multilayer analyzer with linearly graded multilayers is limited in that this type of detector has a limited detection solid angle, restricted by the detector's vertical and horizontal acceptance.

Accordingly, a need remains in the industry for a detector that does not present such limitations in detection and analysis.

SUMMARY OF THE INVENTION

The spectral analyzer described herein addresses many of the deficiencies noted above with respect to the related art.

It is one aspect of this invention to provide a method and apparatus that analyze X-ray fluorescence spectra using synthetic multilayers with improved efficiency and sensitivity.

It is another aspect of this invention to provide a method and apparatus that consists of an array of multilayers to be able to scan X-ray wavelength through a single motor drive.

One further aspect of this invention is to provide a method and apparatus that consists of an array of smaller number of multilayers, which can be linked with a similar unit to form a larger unit.

It is also one aspect of the invention to provide a method and apparatus that analyze X-ray fluorescence spectra using radially graded multilayers having an horizontal acceptance angle about one radian.

Still another aspect of the invention is to provide a method and apparatus that analyze X-ray spectra using an array of graded multilayers having a detection solid angle at several percent to ten percent of $4\pi$.

Further aspects of the invention will be made apparent from the discussion that follows and will be apparent to those skilled in the art.

BRIEF DESCRIPTION OF THE DRAWINGS

The drawings appended hereto illustrate various aspects of apparatuses, methods, and systems in which.

DETAILED DESCRIPTION

While various embodiments are described herein, they are merely illustrative and are not limiting.

Figure 1:
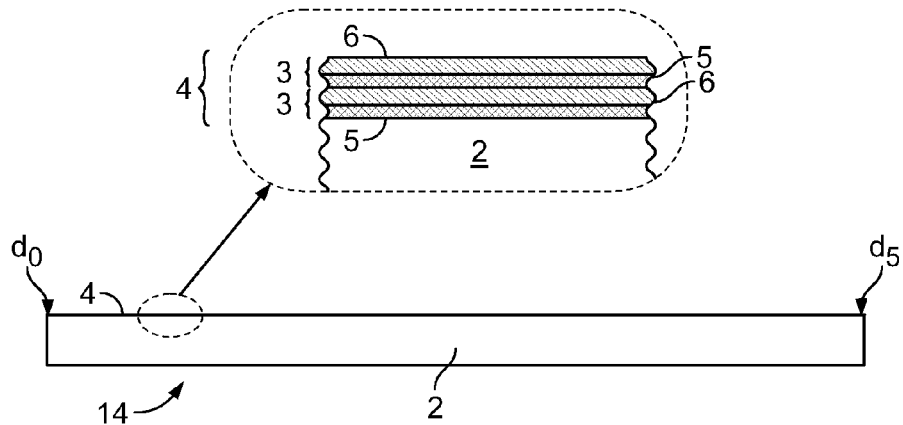
FIG. 1 is a side view of a single mutilayer with an enlarged detail of a portion of the multilayer.

FIG. 1 is a side view of a single radially-graded multilayer 14. The multilayer 14 includes a substrate 2. In the contemplated embodiment of the invention, the substrate 2 may be a material such as glass or silicon (Si) or any variation including glass or silicon. Atop the substrate 2, a plurality of bi-layers 3 are deposited to form a multilayer coating 4. As the name suggests, each bi-layer 3 comprises two layers, a high-Z layer 5 and a low-Z layer 6. The high-Z layer 5 preferably comprises a material made from elements including at least one of tungsten (W) or molybdenum (Mo). The low-Z layer 6 preferably comprises a material made from elements including at least one of silicon (Si) or carbon (C). As a point of reference, high-Z materials are constructed using elements with a high atomic number while low-Z materials are constructed using elements with low atomic numbers. The qualification of "high" atomic number versus "low" atomic number should be understood by those skilled in the art.

It is noted that the present invention is not limited to the materials discussed herein. To the contrary, any alternative material or variation of a specified material is also contemplated to fall within the scope of the invention. With respect to the substrate 2, for example, it is contemplated that any suitable material other than glass or silicon may be used. In addition, there are a wide variety of high-Z and low-Z materials that may be used to construct the bi-layers 3. As a further note, while two bi-layers 3 are illustrated in FIG. 1, a larger or smaller number may be deposited without departing from the scope of the invention.

While not immediately apparent from FIG. 1, it is noted that the thickness of the multilayer coating 4 changes from the leading edge, with a thickness $d_0$ to the trailing edge, with a thickness $d_5$. In the illustrated embodiment, $d_5 > d_0$. Accordingly, the thickness of multilayer coating 4 is not uniform from the leading edge to the trailing edge.

Figure 2:
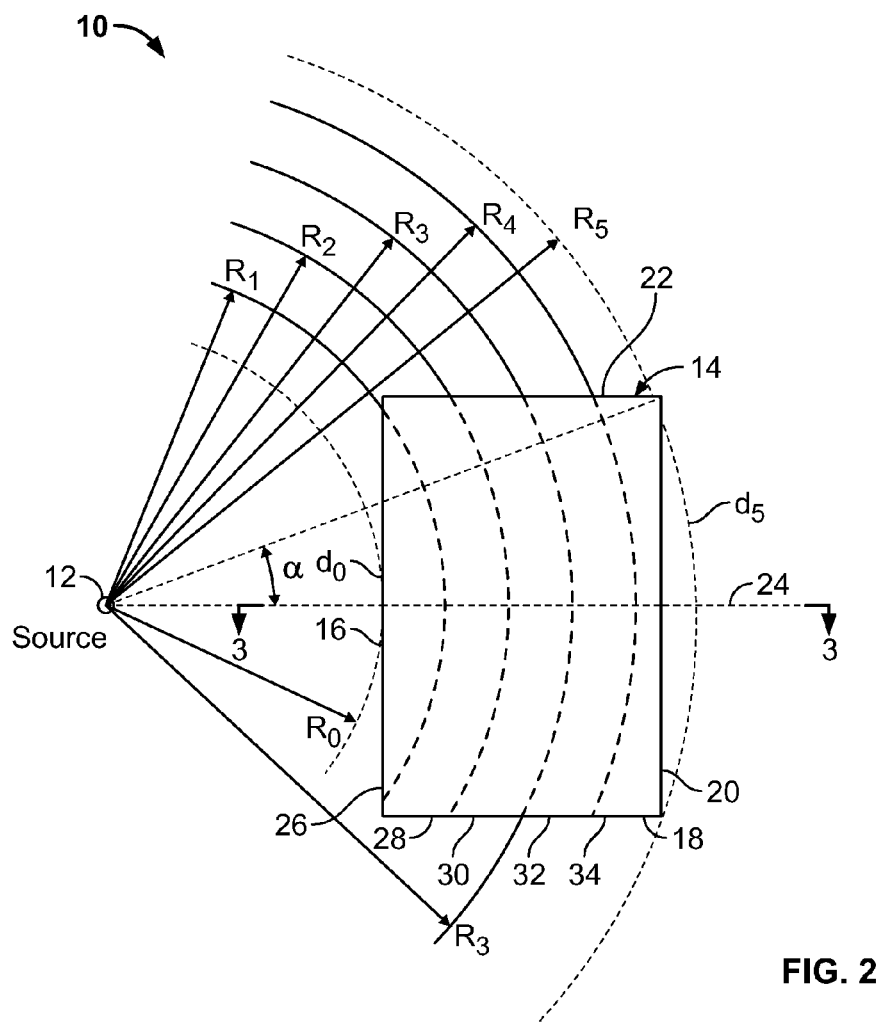
FIG. 2 is a top view of the radially-graded multilayer, where $R_0$ and $R_5$ denote the minimum and maximum d-spacing at the center of the multilayer.

FIG. 2 is a top view illustration of a radially-graded multilayer analyzer geometry 10 defined in relation to a source 12 of electromagnetic radiation. For the radially-graded multilayer analyzer geometry 10, the source 12 preferably is a source of X-ray radiation or at least a portion of the electromagnetic spectrum including some X-rays. As would be appreciated by those skilled in the art, however, the source 12 may emit radiation from other portions of the electromagnetic spectrum.

FIG. 2 also illustrates a top plan view of a single multilayer 14. The multilayer 14 is illustrated as a rectangular plate with first, second, third, and fourth edges 16, 18, 20, and 22, respectively. The first edge 16 is the edge disposed closest to the source 12. The third edge 20 is disposed furthest from the source 12. The second and fourth edges 18, 22 extend between the first and third edges 16, 20, respectively.

As would be appreciated by those skilled in the art, the multilayer 14 need not be rectangular in shape. To the contrary, the multilayer 14 may take any shape suited to the particular analyzer environment.

The thickness of the multilayer 14 is not uniform. Specifically, while the thickness of the substrate 2 is substantially uniform, the thickness of the multilayer coating 4 on the substrate 2 varies differs from the leading edge to the trailing edge, as discussed above. As a result, the thickness of the multilayer 14 changes between the first edge 16 and the third edge 20 in accordance with first through sixth radial band lines, which are labeled $R_0$-$R_5$. In the illustrated embodiment, the radial bands $R_0$-$R_5$ denote regions of the d-spacing for the multilayer 14. For reference purposes, angle α is one half of the horizontal acceptance angle. The radial line 24 is provided to illustrate the approximate location around which the multilayer 14 is symmetrical.

FIG. 2 provides one contemplated overview of the surface contour for the multilayer 14 between the first radial band line $R_0$ and the sixth radial band line $R_5$. For reference purposes, first through the fifth radial bands 26, 28, 30, 32, and 34 are indicated. It is noted that the bands 26, 28, 30, 32, and 34, at least for the embodiment illustrated in FIG. 3, are shown to assist with an understanding of the surface contour for the multilayer 14.

Figure 3:
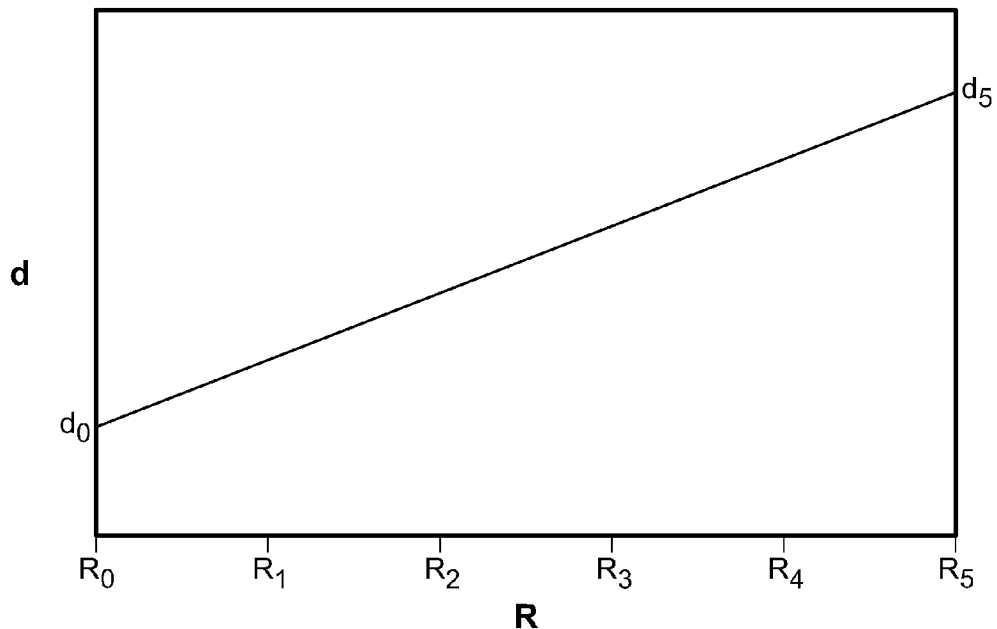
FIG. 3 is a plot illustrating one contemplated d-spacing change from $R_0$ to $R_5$ for the radially-graded multilayer illustrated in FIG. 1.

FIG. 3 provides a graphical plot for one contemplated embodiment of the multilayer 14 of the invention, taken along the line 3-3 in FIG. 2. Here, the thickness of the multilayer coating 4 is illustrated as increasing from the leading edge where the thickness is $d_0$ to the trailing edge where the thickness is $d_5$. Each of the thicknesses $d_0$-$d_5$ is taken at different radial band lines $R_0$-$R_5$, as illustrated in FIG. 2. The change in thickness from $d_0$-$d_5$ is linear, at least in this contemplated embodiment of the invention.

With reference to FIG. 3, the multilayer 14 defines a surface with a grading ratio. In this embodiment, the grading ratio follows the equation:

$$d/d_0 = R/R_0$$

In this equation, d is a d-spacing of the multilayer at R and $d_0$ is the d-spacing at $R_0$. As should be appreciated by those skilled in the art, $d_0$ is a minimum value for the d-spacing for the multilayer 14.

As the illustration also makes clear, the thickness of the multilayer coating 4 is constant at any given radial band line $R_0$-$R_5$. Of course, as should be immediately apparent, the thickness of the multilayer coating 4 may be constant along a line extending parallel to the leading edge 16 of the multilayer 14. Other variations also are contemplated to fall within the scope of the invention.

In one contemplated variation on the embodiment of the multilayer 14, each of the bands 26-34 may define areas with a different linear gradient. In other words, each band 26-34 may define a different d-spacing along a radial direction. In such a case, each band 26-34 would be disposed at a different angle from a horizontal reference line. As should also be appreciated by those skilled in the art, while there are five radial bands 26-34 defined by the multilayer 14, a greater number or a fewer number of bands 26-34 may be employed.

It is noted that each of the radial bands 26-34 need not have a linearly-gradient surface profile. Instead, in cross-section, each radial band 26-34 may define a slightly curved surface. In one additional contemplated embodiment of the invention, the entire surface of the multilayer 14 may define a continuously-curved surface from the leading edge to the trailing edge. Many other variations are possible, as should be apparent to those skilled in the art.

Figure 4:
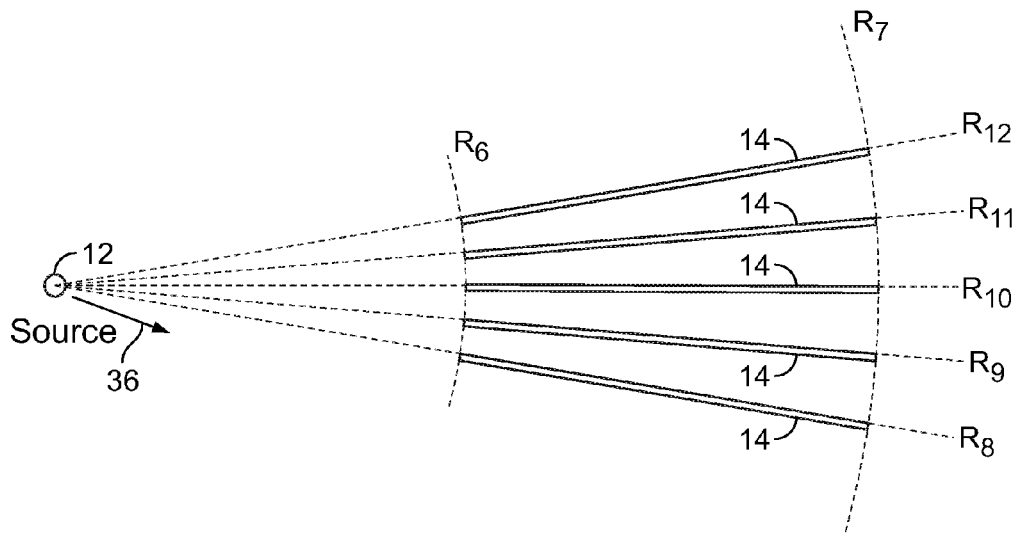
FIG. 4 is a side view from center of the graded multilayer analyzer array incorporating five single multilayers as illustrated in FIG. 1.

Referring to FIG. 4, one contemplated radially-graded multilayer analyzer geometry 10 includes five multilayers 14 radially arranged from the source 12. For purposes of understanding at least this first embodiment of the invention, it is contemplated that the multilayers 14 used in the analyzer geometry 10 are constructed consistently with the illustrations in FIGS. 1-3.

As indicated in FIG. 4, the five multilayers 14 extend between radial band lines $R_6$ and $R_7$. It is noted that radial band lines $R_6$ and $R_7$ correspond to radial band lines $R_0$ and $R_5$, which are shown in FIG. 2. In addition, the five multilayers 14 are disposed along radial lines $R_8$-$R_{12}$, which are centered on the source 12.

As would be appreciated by those skilled in the art, each of the multilayers 14 are identical to one another and share the same geometry as the multilayer 14 illustrated in FIG. 2. Of course, the multilayers 14 need not be identical to one another. Instead, the multilayers 14 may differ from one another both in cross-section (e.g., FIG. 3) and/or in top plan view (e.g., FIG. 1) without departing from the scope of the present disclosure.

FIGS. 2 and 4 illustrate the basic parameters that form the basis for the embodiments of the apparatus described in connection with FIGS. 5-10. Specifically, the radially-graded multilayer analyzer geometry 10 illustrates at least one arrangement of a plurality of multilayers 14 along radial lines extending outwardly, in three-dimensional space, along a travel direction 36 of the electromagnetic photons emitted from the source 12.

In the illustrated embodiment, the source 12 is shown as a point source. However, it should be noted that the source 12 need not be a point source. To the contrary, any other source may be employed. For example, the source 12 may be a line source extending along a direction parallel to edge 16 of the radially-graded multilayer analyzer geometry 10.

Figure 5:
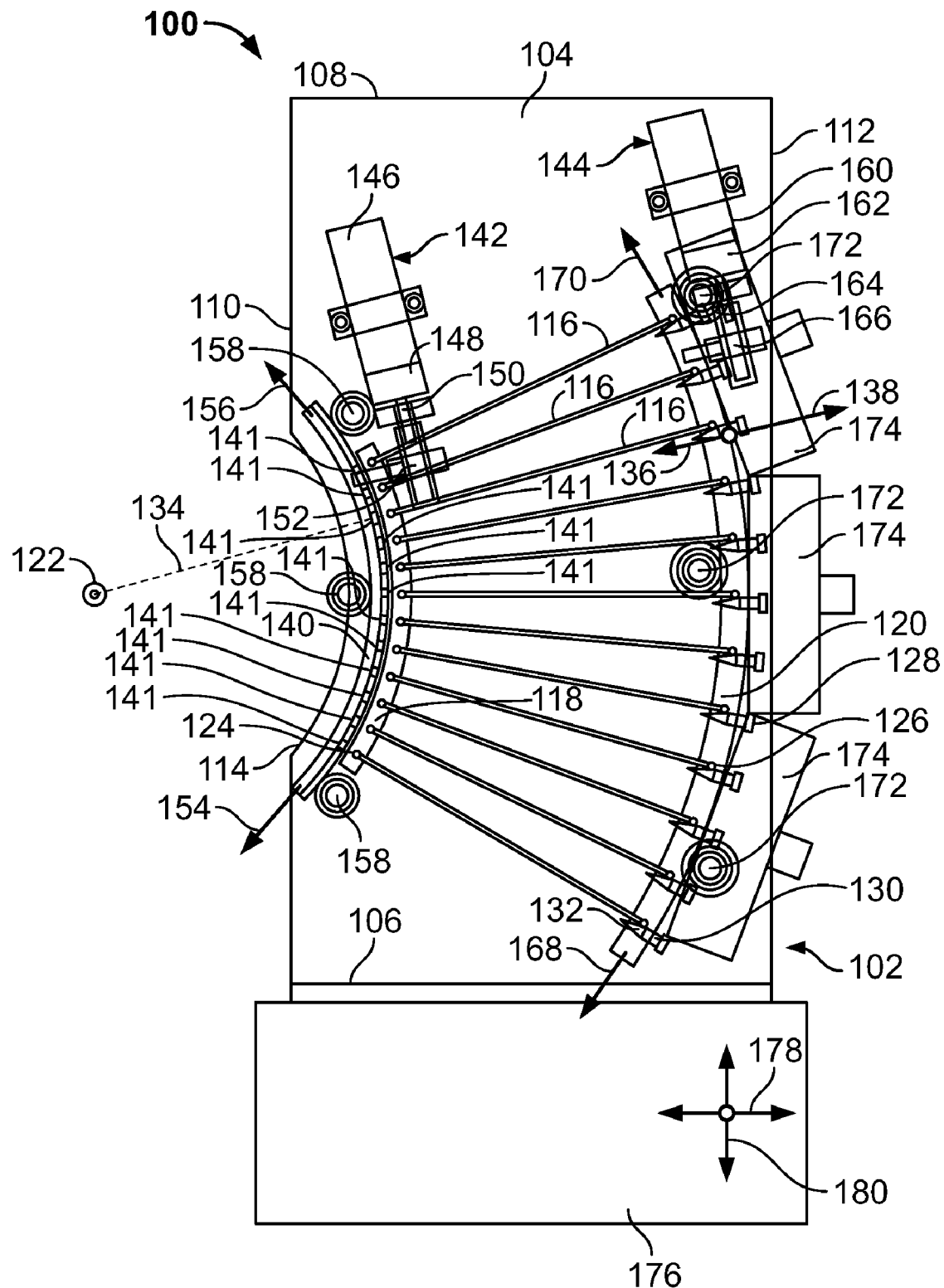
FIG. 5 is a side view illustration of one embodiment of a detector apparatus.

FIG. 5 is a side, elevational view of a first embodiment of a detector apparatus 100.

The detector apparatus 100 includes a housing 102, which comprises two vertical plates 104 disposed side-by-side. Since FIG. 5 is a side view, to facilitate illustration of this embodiment, the front vertical plate has been omitted, leaving only the rear vertical plate 104 visible.

In this first embodiment of the invention, the vertical plates 104 are substantially rectangular plates with a bottom edge 106, a top edge 108, a front edge 110, and a rear edge 112. In FIG. 5, the front edge 110 is shown with a circular cut-out portion 114. The vertical plates 104 may be constructed from a metal material, such as aluminum. Aluminum provides for the construction of a strong, rigid housing 102, but does not add significantly to the overall weight of the detector apparatus 100. As would be appreciated by those skilled in the art, however, this is but one material that may be selected. Other metal materials also may be employed. Alternatively, non-metallic materials may be employed, such as ceramic materials or composites.

Next, as should be appreciated by those skilled in the art, the rectangular shape of the vertical plates 104 is not required to practice the invention. Other shapes may be selected without departing from the scope of the invention. In addition, the circular cut-out portion 114 need not be incorporated into the vertical plates 104. To the contrary, the circular cut-out portion 114 may be omitted altogether. Alternatively, if included, the circular cut-out portion 114 may be of any other shape without departing from the scope of the invention.

In this first embodiment, there are twelve multilayers 116 extending between first and second semi-circular brackets 118, 120. As is apparent from the illustration, the first semi-circular bracket 118 has a smaller radius of curvature than the second semi-circular bracket 120. Both brackets 118, 120, however, share the same center point, which is essentially at the locus of the source 122 of electromagnetic radiation.

With respect to the first and second semi-circular brackets 118, 120, the semi-circular shape assists with the construction of the detector apparatus 100. The shapes of the brackets 118, 120, however, are not required to practice the invention. As would be appreciated by those skilled in the art, any other suitable shape may be employed without departing from the scope of the invention.

The multilayers 116 in the detector apparatus 100 share the same construction as the multilayers 14 illustrated in FIGS. 1-4. However, in keeping with the possibility that the multilayers 116 may have a construction selected from one of the many possible variations discussed above, the reference numeral 116 has been selected to emphasize that the multilayers 116 need not be identical to the multilayers 14 discussed in connection with FIGS. 1-4. Specifically, for this first embodiment, while it is intended for the multilayers 116 to have the surface contour of the multilayers 14 illustrated in FIGS. 1-4, this particular surface contour is not required to practice the invention, as discussed above.

The leading edges 124 of the multilayers 116 are pivotally connected to the first semi-circular bracket 118. Similarly, the trailing edges 126 of the multilayers 116 are pivotally connected to the second semi-circular bracket 120. The pivotal connection of the multilayers 116 to the brackets 118, 120 permits the multilayers to maintain a spatial relationship with respect to one another when either of the first or second brackets 118, 120 are moved, as discussed more fully below.

As may be appreciated from FIG. 5, the leading edges 124 of the multilayers 116 are pivotally fixed to the first semi-circular bracket 118. This means that the leading edges 124 of the multilayers 116 are provided with pins that are inserted into holes in the bracket 118, at least in this contemplated embodiment. As such, the multilayers 116 may pivot with respect to the bracket 118. However, the leading edges 124 cannot be moved (or adjusted) from their positions on the first semi-circular bracket 118. While this construction is illustrated for the detector apparatus 100, it is contemplated that the leading edges 124 of the multilayers 116 may be attached to the first semi-circular bracket 118 via an adjustment mechanism to permit the user to adjust the locations of the leading edges 124 of the multilayers 116, if needed. Other variations may be appreciated by those skilled in the art and are, therefore, intended to be encompassed by the scope of the invention.

The trailing edges 126 of the multilayers 116 are pivotally connected to the second semi-circular bracket 120. However, unlike the leading edges 124, the trailing edges 126 are adjustably mounted to the second semi-circular bracket 120. Specifically, each multilayer 116 connects to the second bracket 120 via an adjustment mechanism 128. The adjustment mechanism 128 provides the user of the detector apparatus 100 with the ability to adjust the angular relationship of each multilayer 116 with respect to others of the multilayers 116. Accordingly, the overall operation of the detector apparatus 100 may be adjusted to meet the demands of a particular analysis.

The adjustment mechanisms 128 are contemplated to be simple in design while providing the user with the ability to make small positional adjustments of the trailing edges 126 of the multilayers 116. As illustrated in FIG. 5, the adjustment mechanisms 128 each comprise a screw 130 with a tapered tip 132. The tapered tip 132 is connected to the trailing edges 126 of the multilayers via a suitable connector (not illustrated). As the screw 130 is rotated, the tapered tip 132 will move radially inward 136 or radially outward 138, depending on the direction in which the screw 130 is rotated. The tapered tip 132 will act on the trailing edge 126 of the multilayer 116 to alter to angular position of the multilayer with respect to the radial line 134 centered on the source 122.

It is expected that a user will not need to adjust the positions of the multilayers 116 with respect to one another after an initial alignment. Specifically, as noted above, the multilayers 116 are intended to be positioned along their respective radial lines 134 such that they are evenly spaced from one another. As a result, while it may be necessary for a user to make initial adjustments of the trailing edges 126 of the multilayers 116 for a particular set of detection parameters, these "settings" are not expected to need adjustment on a continual basis. Of course, the construction of the detector apparatus 100 is such that adjustments may be made to the positions of the trailing edges 126 of the multilayers 116 at any time, as needed.

It is contemplated in one possible variation of the detector apparatus that the trailing edges 126 of the multilayers may be connected to the second semi-circular bracket 120 by a remotely-operated adjustment mechanism. For example, the adjustment mechanism may be electrically operated via a computer or other suitable processor. The same configuration may be applied to the leading edges 124 of the multilayers with respect to the first semi-circular bracket 118, as should be appreciated by those skilled in the art.

A screen 140 is disposed ahead of the first circular bracket 118. Screen 140 includes a number of slits 141, each slit 141 corresponding to a multilayer 116. A screen drive 142 is connected to the screen 140 so that the screen position may be adjusted. Similarly, an angular drive 144 is connected to the second circular bracket 120 to move the second bracket 120.

The screen drive 142 includes a motor 146 with an integrated a gearbox 148 and a shaft 150. The gearbox 148 connects to the screen 140 via a linkage 152. As a result, when the motor 146 is actuated, circular motion is transferred via the gearbox 148 to the shaft 150. This circular motion is transferred to the screen 140 via the linkage 152 to move the screen 140. It is contemplated that the screen 140 will be moved in an arcuate fashion along the radius of curvature in a clockwise 154 or a counterclockwise 156 direction. To permit this rotational motion, the screen 140 is mounted between the vertical plates 104 via spindles or bearings 158, three of which are illustrated in FIG. 5. The spindles 158 may be substituted with any suitable alternative, as should be appreciated by those skilled in the art. It is noted that the movement of the screen 140 permits adjustment of the vertical acceptance of the impingent electromagnetic rays from the source 122, as also should be appreciated by those skilled in the art.

In the embodiment illustrated in FIG. 5, the screen drive 142 controls only movement of the screen 140. However, in one contemplated variation on the detector apparatus 100, the screen drive 142 also could be connected to the first semi-circular bracket 118 to adjust the position of that bracket 118 and also the leading edges 124 of the multilayers 116. In still another contemplated embodiment, the bracket 118 could be provided with its own, separate drive mechanism. Other variations are also contemplated, as should be appreciated by those skilled in the art, and these variations are also intended to be encompassed by the scope of the invention.

The angular drive 144 shares the same construction as the screen drive 142. Specifically, as illustrated, the angular drive 144 includes a motor 160 with an integral gearbox 162 and a shaft 164. The gearbox 162 connects to the second semi-circular bracket 120 via a linkage 166. As a result, when the motor 160 is actuated, circular motion is transferred via the shaft 164 to the linkage 166. This circular motion is transferred to the second bracket 120 via the linkage 166 to move the second bracket 120. It is contemplated that the second bracket 120 will be moved in an arcuate fashion along its radius of curvature in a clockwise 168 or a counterclockwise 170 direction. To permit this rotational motion, the second bracket 120 is mounted between the vertical plates 104 via spindles or bearings 172, three of which are illustrated in FIG. 5. The spindles 172 may be substituted with any suitable alternative, as should be appreciated by those skilled in the art. It is noted that the movement of the second bracket 120 permits collective adjustment of the trailing edges 126 of the multilayers 116.

The multilayers 116 interact with the high energy photons from the source 122 to select the energy of the photons that are permitted to impinge upon detectors 174. Via diffraction, among other physical parameters associated with the multilayers 116, the multilayers 116 permit selection of the energy of the photons that impinge upon the detectors 174.

The angular position of the multilayers 116 with respect to the direction of the impingent electromagnetic radiation is a factor in determining what energy (or energies) of the photons will pass the multilayers 116 and impinge upon the detectors 174. Accordingly, to change the magnitude of the energy (or energies) of the impingent photons, all that needs to be done is to alter the angular orientation of the multilayers with respect to the impingent photons. The angular drive 144 shifts the multilayers 116 to change the energy (or energies) of the photons impingent on the detectors 174. As a result, by rotating the second bracket 120 through a series of angular positions, a wide range of photons of different energies are permitted to impinge upon the detectors 174. In this fashion, a spectrum of the distribution of photons at different energies may be generated.

As FIG. 5 illustrates, three large area detectors 174 are positioned adjacent to the multilayers 116. The detectors 174 may be any one from a large variety of different types. For example, the detectors 174 may be photodiodes, ionized gas radiation detectors, scintillation detectors, etc. These types of detectors typically have a saturation at a very high photon flux.

It is noted that traditional scintillation detectors detect the energies of impingent photons in addition to the quantity of those photons, thereby permitted the creation of a graph representative of the spectrum of the photons impingent thereon.

By the present disclosure, it should be apparent to those skilled in the art that the detectors 174 are relied upon to quantify the number of impingent photons. It is unnecessary to determine the energies of the respective photons since the positions of the multilayers 116 permits selection of the energies of the photons impingent thereon in a predetermined energy band, preferably a narrow energy band. It is for this reason, among others, that the detector apparatus and system of the present disclosure does not have a low saturation limit, as with prior art scintillation detectors.

Returning to the detector apparatus 100 in FIG. 5, an X-Z stage 176 is positioned beneath the vertical plates 104. The X-Z stage 176 permits adjustment of the vertical plates 104 in both the X direction 178 and the Z direction 180. With these adjustments, it is possible to align the detector apparatus 100 with the source 122 to optimize the operation of the device as a whole.

Figure 6:
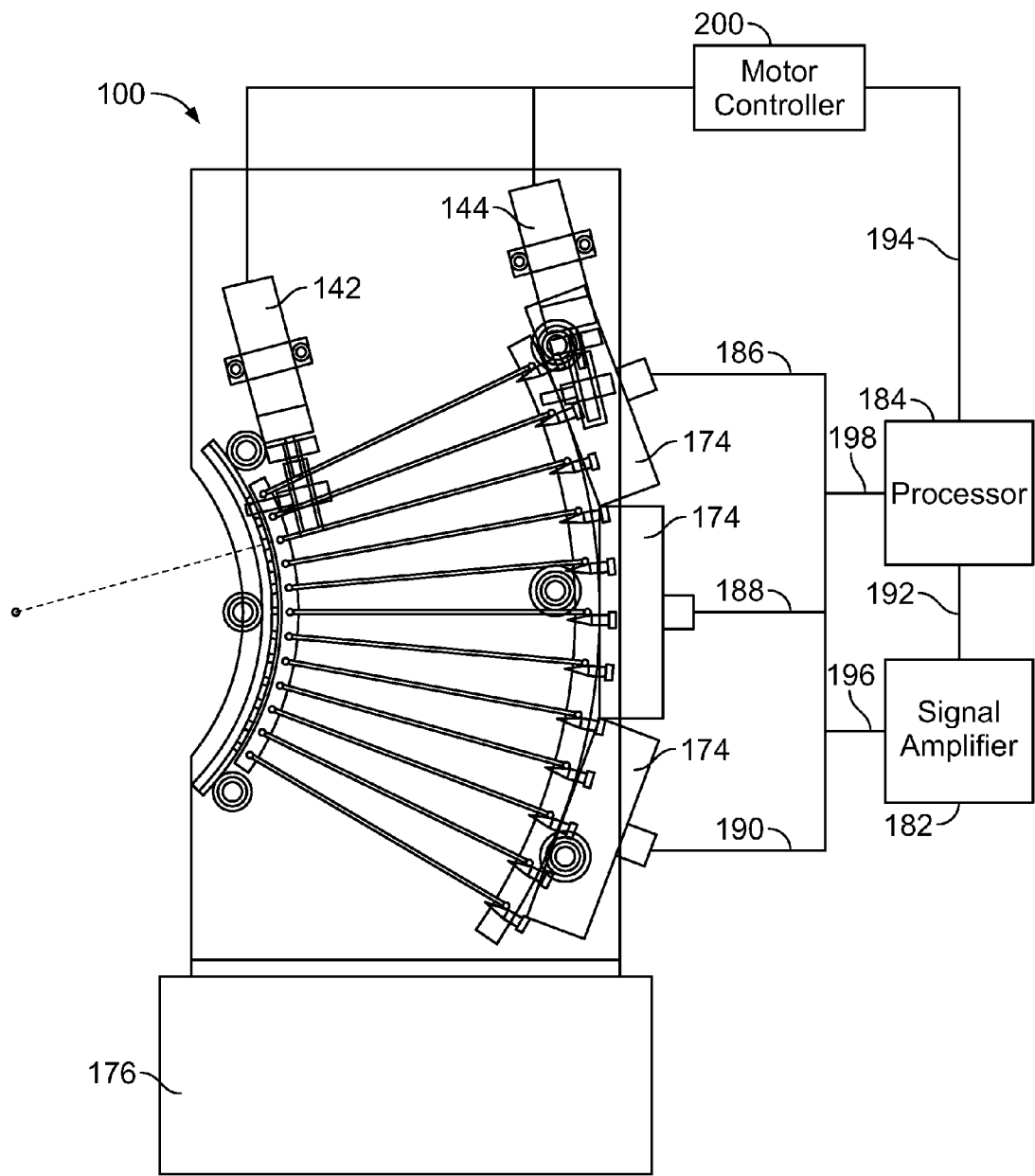
FIG. 6 is a side view schematic illustration of the detector apparatus illustrated in FIG. 5, also showing selected, associated componentry.

FIG. 6 is a schematic illustration of the detector apparatus 100 as may be connected to peripheral equipment including a signal conditioning module 182, possibly including a signal amplifier, and a processor 184, such as a personal computer. As should be appreciated by those skilled in the art, the processor 184 may be any type of device that can process the signals from the detectors 174 via the signal conditioning module 182 and generate instructions for operation of the screen drive 142 and the angular drive 144 via the motor controller 200. Processor 184 may also store the signals received from the detectors 174 and the corresponding positions of screen drive 142, angular drive 144 and provide direct communication or other means of data transfer to equipment the user employs for further processing of the signals from the detectors 174 and related positions of screen drive 142 and angular drive 144.

As illustrated in FIG. 6, the three detectors 174 are connected to output communication lines 186, 188, 190. These output communication lines 186, 188, 190 carry the signals to the signal conditioning module 182 and to the processor via communication links 196, 198. Among other processing functions as would be appreciated by those skilled in the art, the signal conditioning module 182 amplifies the signals, converts them to digital pulses, and presents these signals to the processor 184 via the communication link 192. The processor 184 receives the signals from the signal conditioning module 182 and from the detectors 174, saves the signals as needed, and generates an output control signal to control the operation of one or both of the screen drive 142 and the angular drive 144 via the communication link 194 to the motor controller 200.

As should be appreciated by those skilled in the art, the signal conditioning module 182 is not required to practice the invention. If the detectors 174 generate sufficiently robust signals of a suitable format, the signals may be provided solely to the processor 184. As also should be appreciated by those skilled in the art, a multiplexer may be required to process the signals from the plural detectors 174. In addition, a controller 200 may not be needed to provide control signals to the screen drive 142 and the angular drive 144. Those skilled in the art should appreciate that other variations are also contemplated to fall within the scope of the invention.

Figure 11:
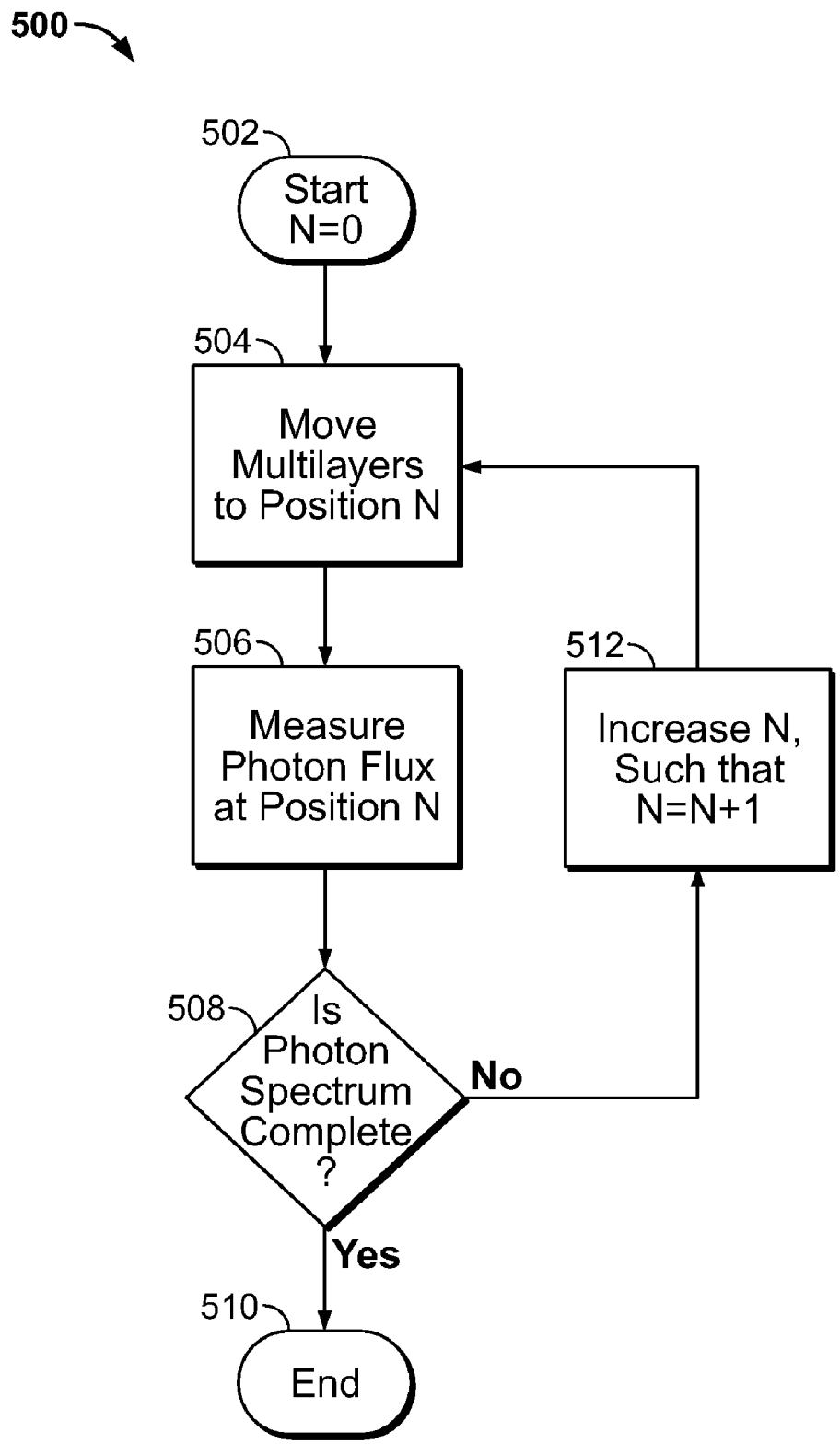
FIG. 11 provides a flow diagram of one contemplated method for operation of the detector apparatus.

Reference is now made to FIG. 11, which provides a diagram of one contemplated, iterative method 500 associated with the operation of the detector apparatus 100. The method begins at 502, where the iterative count is set to N=0. The multilayers 116 are positioned at an initial operative position at 504 by operation of the angular drive 144. As noted above, the angular drive is controlled by signals from the processor 184.

At the initial position, the multilayers 116 permit photons, at one predetermined energy level or a narrow range of predetermined energy levels, to pass to the detectors 174. Since one definition of a flux of photons is defined as the number of photons per unit of time, such as a second, the detectors 174 detect the number of impingent photons for a period of time, as indicated by 506. The detector count will continue for a predetermined period of time, thereby resulting in a total count of photons for that predetermined period of time. The count information is passed from the detectors 174 to the processor 184 via the signal conditioning module 182, if signal conditioning module 182 is included as a part of the supporting componentry for the detector apparatus 100.

After the processor 184 records the count of photons at the initial position of the multilayers 116, the processor 184 determines if the photon spectrum is complete at 508. If so, the method is stopped at 510. If the spectrum is not complete, the method proceeds to 512, where the iterative count N is increased by one, N=N+1. The processor then generates a signal, which is sent to the motor controller 200 controlling the angular drive 144, to move the multilayers to a position defined by the iterative count N=1. The process 506, 508 then repeats iteratively until the full spectrum is collected.

Figure 7:
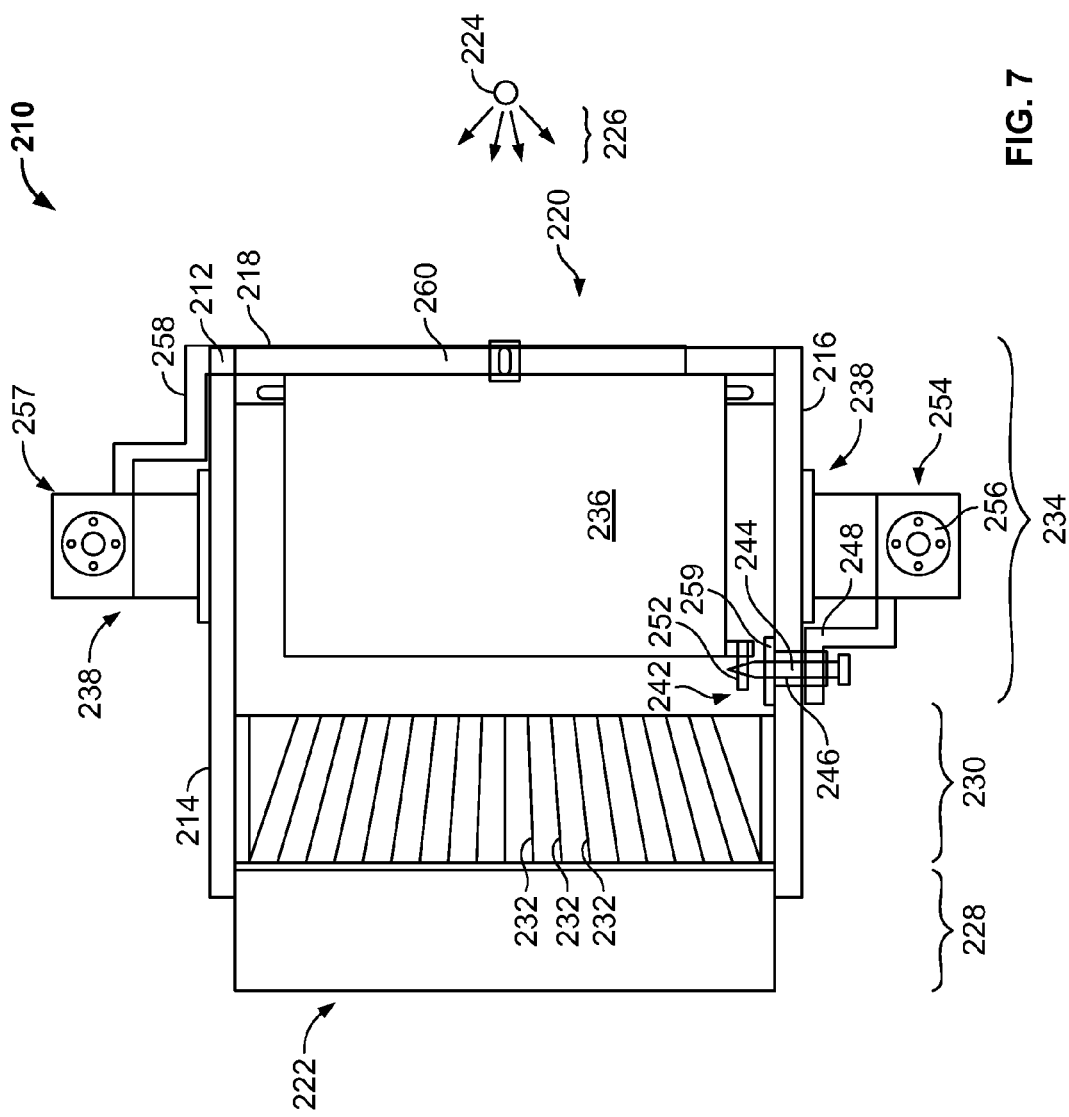
FIG. 7 is a top, plan view of another embodiment of a detector apparatus.

FIG. 7 provides a top, plan view of a second contemplated embodiment of a detector apparatus 210 incorporating the radially-graded multilayer analyzer geometry 10 illustrated in FIGS. 2 and 4. The detector apparatus 210 includes a housing 212 with a first side wall 214, a second side wall 216, and a third wall 218. In the illustrated embodiment, the first side wall 214, the second side wall 216, and the third wall 218 form essentially a rectangular box. As would be appreciated by those skilled in the art, the housing 212 need not be rectangular but may take any alternative suitable shape as required by a particular environment.

As points of reference, the detector apparatus 210 illustrated in FIG. 7 has a source side 220 and a detector side 222. The source side 220 of the detector apparatus 210 faces a source 224 of photons 226, the travel paths of which are represented by the arrows 226 in FIG. 7. The detector side 222 of the detector apparatus 210 will be described in greater detail below.

The detector apparatus 210 includes a collection portion 228, also referred to as an area detector portion 228, which is disposed at the detector side 222 of the apparatus. The photons 226 are collected by the collection portion 228, which is positioned adjacent to a collimating portion 230. Collimating slits 232 are arranged in the collimating portion 230 to collimate the photons 226 in their travel direction from the source side 220 to the detector side 222 of the detector apparatus 210. In the illustrated embodiment, the collimating slits 232 are a series of nineteen plates arranged in a specific, vertical pattern within the collimating portion 230. As illustrated and as would be understood by those skilled in the art, the collimating slits or plates 232 are angularly disposed within the collimating portion 230 with respect to one another. While one particular arrangement of the collimating slits or plates 232 is illustrated, it should be understood that the detector apparatus 210 is not limited solely to this particular arrangement. Instead, any number of different configurations for the collimating slits or plates 232 may be selected depending upon the background, the source 224, or the energies of the photons 226, as would be appreciated by those skilled in the art.

A multilayer portion 234 is positioned adjacent to the collimating portion 232 of the detector apparatus 210. The multilayer portion 234 of the detector apparatus 210 contains at least one multilayer 236. The multilayer 236 may have the same geometry as the multilayers 14 described in connection with FIGS. 2 and 4 or the multilayer 236 may have a different geometry. Accordingly, the multilayer 236 is provided with a different reference number to emphasize this potential difference.

Consistent with the discussion of the multilayers 14 described in connection with FIGS. 2 and 4, in the detector apparatus 210, there are preferably five multilayers 236 arranged in the same radial geometry as illustrated in FIGS. 2 and 4. Accordingly, the following discussion presumes the placement of five multilayers 236 in the multilayer portion 234 of the detector apparatus 210. As noted above, a greater number or a fewer number of multilayers 236 may be employed, as would be appreciated by those skilled in the art.

As noted, while the detector apparatus 210 may be designed to include only one multilayer 236, in the embodiment illustrated, there are five multilayers 236 radially stacked with respect to one another. The stacked arrangement of the five multilayers 236 is also illustrated in FIG. 8.

As a general rule, the greater the number of multilayers 236, the greater the ability of the detector apparatus 210 to differentiate between the different energies of the photons 226 impingent thereon. Of course, as also would be recognized by those skilled in the art, the greater the number of multilayers 236, the larger the detector apparatus 210 and the more expensive the detector apparatus 210 becomes to construct. Therefore, when selecting the number of multilayers 236 for a particular detector apparatus 210, a balance is established between the sensitivity and efficiency of the detector apparatus 210 and the cost associated with its construction.

Returning to FIGS. 7 and 8, the housing 212 is fixedly disposed on a support 238 disposed atop a base 240. A ring 259, similar to bracket 120 in FIG. 5, is mounted to the side plate 216 through bearings. One or more adjustment screws 244 are mounted on the ring 259. The ring 259 is connected to the motor drive 256 through the arm 248. All the multilayers 236 rest on the adjustment screw(s) 244 through one or more pins 252. This permits the rotational motion for all the multilayers 236. The adjustment screw(s) 244 and the pin(s) 252 together make up an adjustment mechanism 242. While included in this embodiment, it is contemplated that the detector apparatus 210 may not include the adjustment mechanism 242. The requirements of the particular environment in which the detector apparatus 210 will function (in addition to other factors) will play a role in the inclusion or exclusion of the adjustment mechanism 242, as would be appreciated by those skilled in the art.

Figure 8:
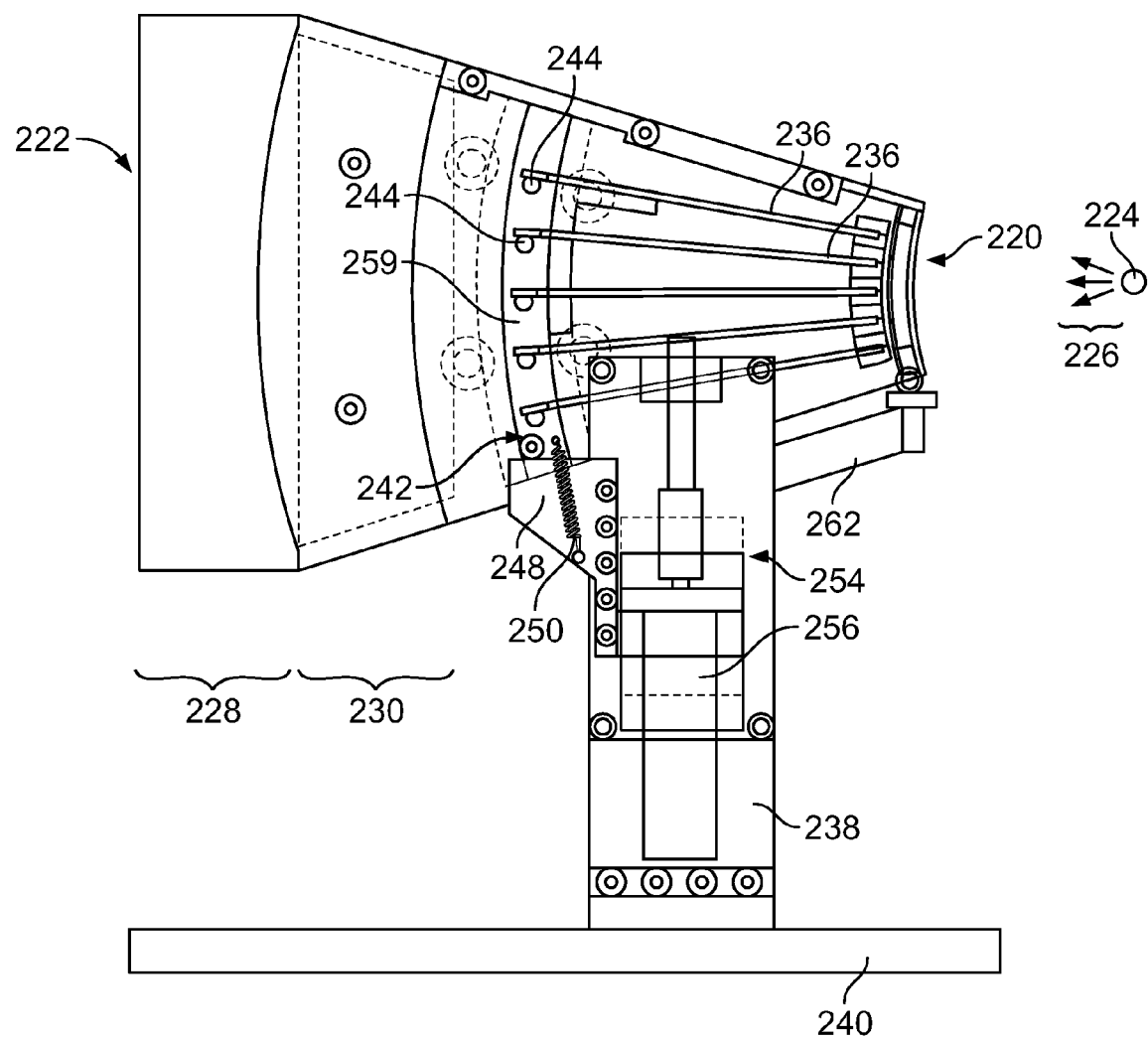
FIG. 8 is a side, elevational view of the embodiment of the detector apparatus as illustrated in FIG. 7.

As illustrated in FIG. 8, the adjustment screw 244 rests atop an armature 248 that extends from the support 238 beneath the detector apparatus 210. With reference to FIG. 7, the adjustment screw 244 extends from the armature 248 through the hole 246 in the housing 212 to the pin 252. A spring 250 extends between the armature 248 and the ring 259. The spring 250 helps to hold the ring 259 in a suitable positional relationship with respect to the armature 248.

In the illustrated embodiment, the support 238 includes an angular drive mechanism 254 with a drive motor 256. The angular drive mechanism 254 connects between the support 238 and the ring 259 via the adjustment mechanism 242. In operation, the drive motor 256 drives a screw (or other suitable adjustment portion) that raises or lowers the armature 248. By raising or lowering the armature 248, the ring 259 may be adjusted in very small angular increments. In this fashion, the ring 259 is moved in a manner similar to that of the second semi-circular bracket 120 described above.

As may be appreciated from the foregoing discussion, the adjustment mechanism 242 and the angular drive mechanism 254 cooperate to provide angular adjustment for the ring 259. Since the multilayers 236 are connected pivotally to the ring 259, movement of the ring 259 adjusts the angular positions of the multilayers 236, as in the previous embodiment. In addition, while not illustrated in connection with this embodiment, the multilayers 236 may be connected to the ring 259 via an additional adjustment mechanisms 128, like the ones described in connection with the previous embodiment.

In the illustrated embodiment, a screen drive mechanism 257 is positioned on the side of the housing 212 with the first side wall 214. The screen drive mechanism 257 is connected to a screen armature 258 that is connected to a screen 260 at the source side 220 of the detector apparatus 210. The screen drive mechanism 257 operates to adjust the position of the screen 260, as needed.

It is noted that the screen 260 is moveable with respect to the housing 212. In particular, the screen 260 moves for vertical acceptance of the impingent electromagnetic rays 226 from the source 224.

Returning to FIG. 8, a rear housing support arm 262 extends beneath the multilayer portion 234 of the housing 212 to provide the actuation for screen 260.

Figure 9:
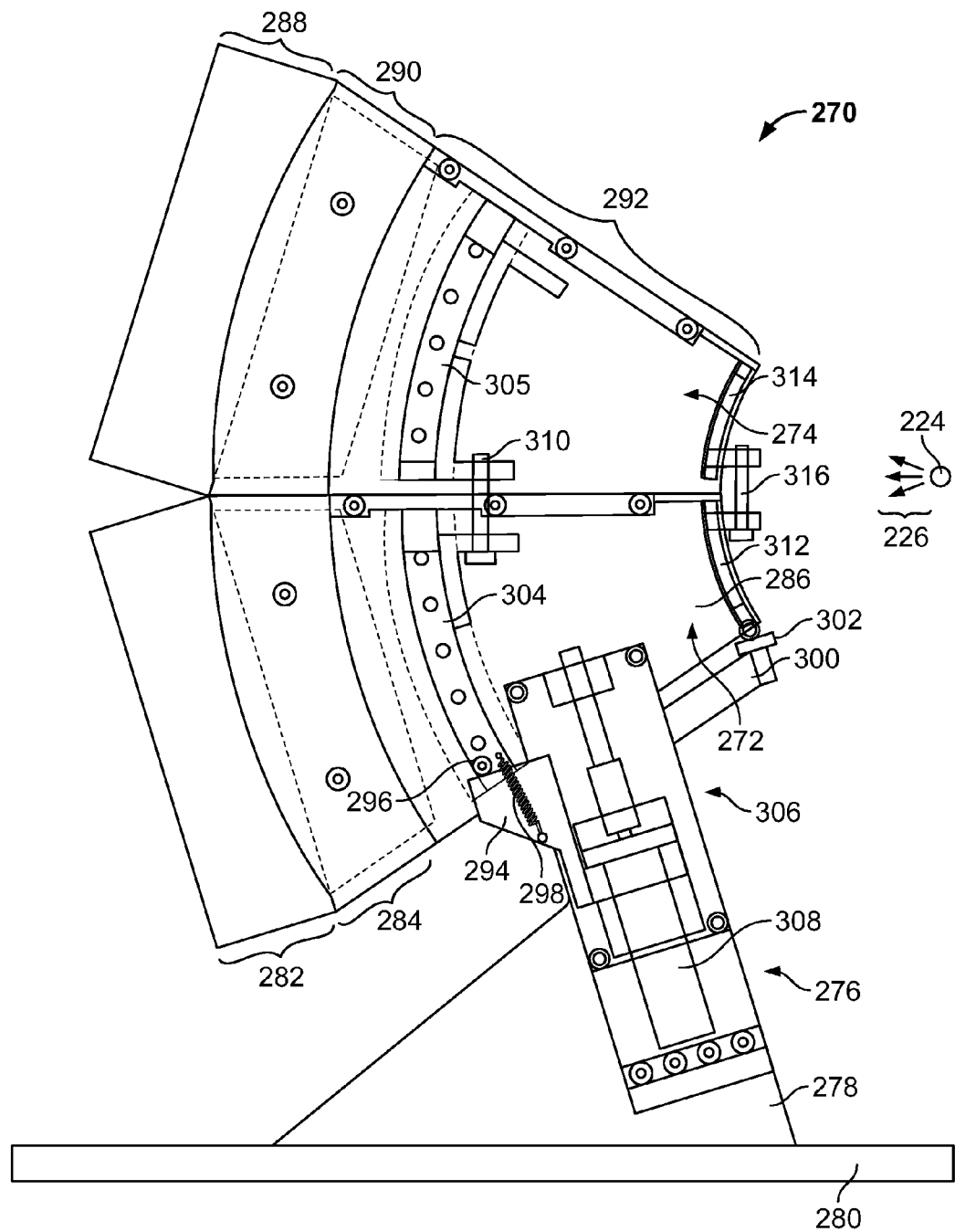
FIG. 9 is a side, elevational view of yet another embodiment of the detector system.

FIG. 9 is a side view elevational illustration of a third embodiment of a detector apparatus 270. The detector apparatus 270 shares many common features described in connection with the detector apparatus 210 illustrated in FIGS. 7 and 8. In fact, the detector apparatus 210 contemplates a modular construction so that two or more detector apparatuses 210 may be combined to form a larger apparatus, such as the detector apparatus 270.

A modular construction for the detector apparatus 270 offers several advantages with respect to the cost of construction. One advantage of a modular construction lies in the potential for manufacturing and offering for sale modules that can be purchased by a customer to add to an existing detection apparatus, such as the detection apparatus 210.

As is immediately apparent, the detector apparatus 270 is a larger version of the detector apparatus 210, in that the detector apparatus 270 includes two separate detector housings, a first detector housing 272 and a second detector housing 274. In the embodiment illustrated in FIG. 9, the first detector housing 272 is connected to and is positioned adjacent to the second detector housing 274.

The first detector housing 272 is associated with a primary detector and the second detector housing 274 is associated with a secondary detector. As would be appreciated by those skilled in the art, additional detector housings (and additional detectors) may be added to the basic structure illustrated in FIG. 9 without departing from the scope of the present disclosure.

The detector apparatus 270 sits atop a support 276 that combines an angular bracket 278 with a base 280. As illustrated, to accommodate both the first detector housing 272 and the second detector housing 274, the support bracket 278 is angled with respect to the base 280. As would be appreciated by those skilled in the art, an angled support bracket 278 is not required. Variations on the support 276 are, therefore, intended to fall within the scope of the present disclosure.

As with the detector apparatus 210, the first detector housing 272 defines at least three separate regions, a collection portion 282, a collimation portion 284, and a multilayer portion 286. Similarly, the second detector housing 274 defines a collection portion 288, a collimation portion 290, and a multilayer portion 292. As with the detector apparatus 210, the collimation portions 284, 290 include collimation slits or plates (although they are not illustrated in FIG. 9). In addition, the multilayer portions 286, 292 include one or more multilayers (also not shown in this illustration).

As with the detector apparatus 210, the detector apparatus 270 includes an armature 294 that engages one or more adjustment screws 296. The adjustment screw(s) 296 behave in the same manner as the adjustment screws 244. As with the detector apparatus 210, a spring 298 provides a biasing force.

As illustrated in FIG. 9, the detector apparatus 270 includes a support armature 300, which includes a support surface 302. The armature 300 and support surface 302 assist in providing the actuation for screens 312 and 314.

In addition, as with the detector apparatus 210, the detector apparatus 270 includes an angular drive mechanism 306 connected between the support 276 and a first ring 304 and a second ring 305 to provide fine control over the angular position of the multilayers (not shown in this illustration). The angular drive mechanism 306 includes a drive motor 308 to provide fine angular adjustment for the rings 304, 305.

Also illustrated in FIG. 9 is a ring connector 310 that connects the rings 304 and 305 to one another. In addition, to connect the screens 312, 314 together, a screen connector 316 is provided. In the illustrated embodiment, the ring connector 310 and the screen connector 316 preferably are screw-type connectors to provide fine control for the respective positions of the rings 304 and 305 and the screens 312, 314. As would be appreciated by those skilled in the art, other adjustment mechanisms may be employed. In addition, a screen drive (not shown) is provided for angular adjustment of the screens 312, 314, as in the previous embodiment.

Figure 10:
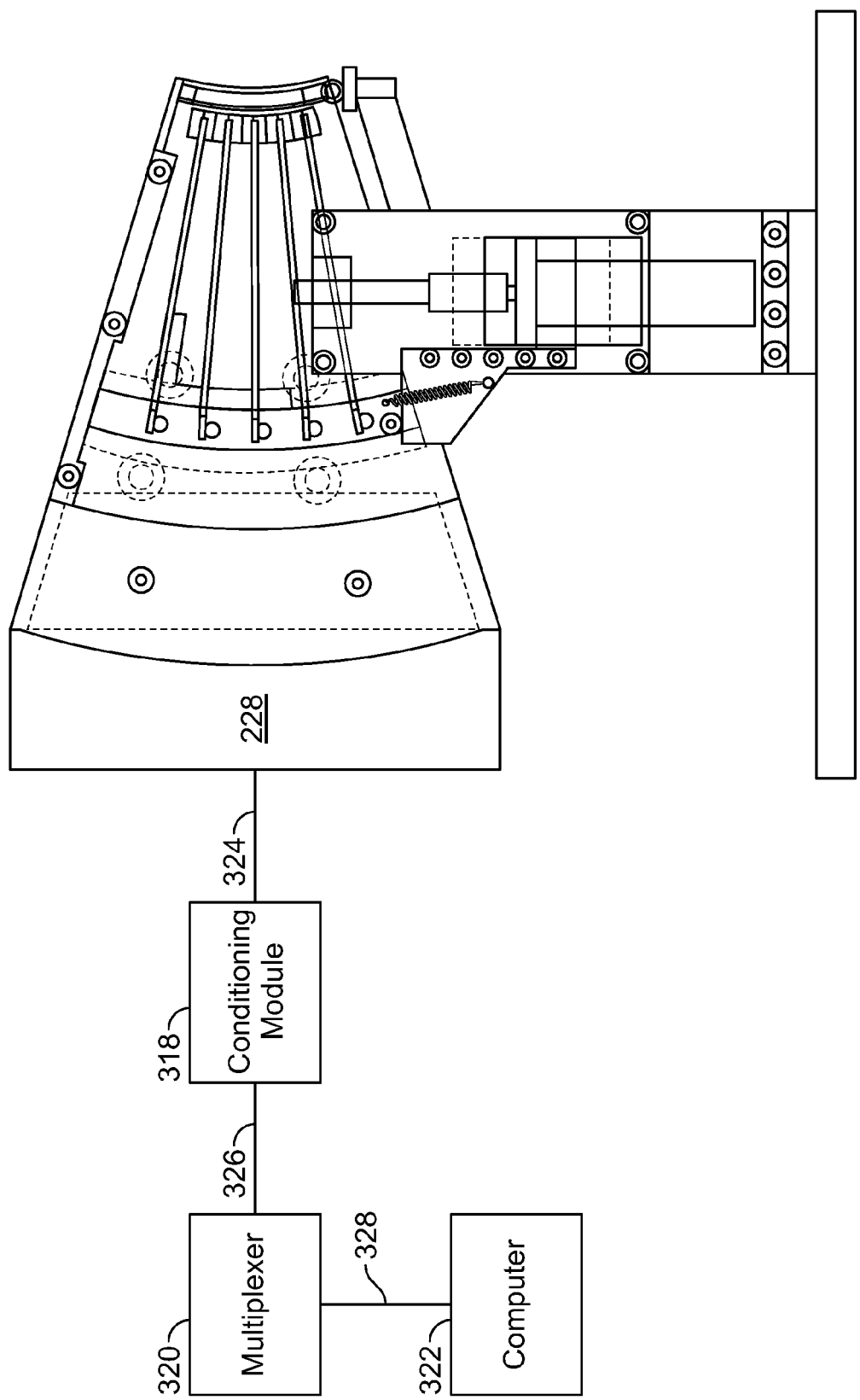
FIG. 10 is a schematic diagram of the embodiment of the detector system illustrated in FIG. 8, showing selected, associated componentry.

FIG. 10 provides a high-level, architectural overview of a detector system that incorporates the detector apparatus 210 described in connection with FIGS. 7 and 8. As illustrated, raw data from the detection portion 228 is directed to a signal conditioning module 318. From the signal conditioning module 318, the data may be sent to a multiplexer 320. From the multiplexer 320, the data may be sent to a computer 322 or other suitable device with a processor. As would be appreciated by those skilled in the art, the computer 322 may be connected or contain additional hardware such as memory, etc. that may be employed to store the data collected.

As also illustrated in FIG. 10, a first communication link 324 connects the detector apparatus 210, 270 to the signal conditioning module 318. Electrical signals generated by the detector apparatus 210, 270 are provided to the signal conditioning module 318, which produce digital signals. The digital signals are then transmitted to the multiplexer 320 via a second communication link 326. A third communication link 328 carries the multiplexed signals to the processor 322. As would be appreciated by those skilled in the art, the communication links 324, 326, 328 may be either wired or wireless links.

While not illustrated in detail, the multilayers 236 may be constructed from any of a number of materials. In particular, the multilayers 236 are constructed to have either a linearly or a radially gradient surface to improve energy detection of photons 226. While multilayers 236 with a linearly gradient surface are acceptable for the detector apparatus 210, 270, multilayers 236 with radially gradient surfaces are preferred because they have improved detection efficiency and resolution across a wide energy spectrum, for example, from about 1 keV to about 10 keV.

As would be appreciated by those skilled in the art, there are numerous variations on and equivalents to the embodiments described herein that may be employed without departing from the scope of the present disclosure.

DOCUMENTS CITED

U.S. Pat. No. 5,799,056 August 1998 Gutman

Energy-Resolving X-ray Fluorescence Detection Using Synthetic Multilayers, *J. Synchrotron Rad* 5 (1998) pp. 1227-1234.

We claim:

1. A detector apparatus for electromagnetic radiation originating from a source, the detector apparatus comprising:
    a housing;
    at least one multilayer disposed within the housing, the at least one multilayer defining a leading edge and a trailing edge, wherein the at least one multilayer is adapted to interact with a plurality of high-energy photons within the X-ray portion of the electromagnetic spectrum, impingent from the leading edge, to permit passage of photons of at least one selected from a plurality of different energies;
    a first securement bracket disposed within the housing, wherein the at least one multilayer is pivotally fixed to the first securement bracket at a position adjacent to the leading edge;
    a second securement bracket disposed within the housing, wherein the at least one multilayer is adjustably supported by the second securement bracket at a position adjacent to the trailing edge;
    at least one detector disposed adjacent to the trailing edge of the at least one multilayer, wherein the detector is adapted to detect the impingent high-energy photons after interaction with the at least one multilayer; and
    at least one adjustment mechanism operatively connected to the second securement bracket, wherein the at least one adjustment mechanism adjusts the position of the second securement bracket to alter an angular position of the at least one multilayer wherein the at least one multilayer is oriented along a radial line extending outwardly from the source.

2. The detector apparatus of claim 1, wherein the at least one multilayer comprises a plurality of multilayers.

3. The detector apparatus of claim 1, wherein the at least one multilayer comprises a linearly gradient surface.

4. The detector apparatus of claim 1, wherein the at least one multilayer comprises a radially gradient surface.

5. The detector apparatus of claim 4 wherein the at least one multilayer has a body defining a surface with a grading ratio, wherein the grading ratio follows the equation:

$$d/d_0 = R/R_0$$

wherein d is a d-spacing of the multilayer at a distance R from a center point, and
    wherein $d_0$ is the d-spacing at $R_0$, which is a minimum value for the at least one multilayer.

6. The detector apparatus of claim 1, further comprising:
    a collimating portion defined within the housing adjacent to the at least one multilayer to collimate the plurality of impingent high-energy photons after interaction with the at least one multilayer; and
    a plurality of collimating plates disposed in the collimating portion to facilitate collimation of the plurality of impingent high-energy photons.

7. The detector apparatus of claim 1, wherein the at least one adjustment mechanism comprises a motor operative on the second securement bracket.

8. The detector apparatus of claim 1, further comprising:
    a processor connected to the at least one detector to receive signals generated by the detector and generate a control signal to operate the at least one adjustment mechanism.

9. The detector apparatus of claim 8, wherein the processor is adapted to generate a spectrum associated with the plurality of high-energy photons.

10. The detector apparatus of claim 1, further comprising:
    a screen disposed adjacent to the leading edge of the at least one multilayer, wherein the screen is adapted to adjust the vertical acceptance of the impingent high-energy photons.

11. The detector apparatus of claim 10, further comprising:
    a second adjustment mechanism operatively connected to the screen, wherein the second adjustment mechanism adjusts the position of the screen.

12. A detection system, comprising:
    a detector apparatus including
        a housing;
        at least one multilayer disposed within the housing, the at least one multilayer defining a leading edge and a trailing edge, wherein the at least one multilayer is adapted to interact with a plurality of high-energy photons within the X-ray portion of the electromagnetic spectrum, impingent from the leading edge, to permit passage of photons of at least one selected from a plurality of different energies,
        a first securement bracket disposed within the housing, wherein the at least one multilayer is secured to the first securement bracket at a position adjacent to the leading edge, a second securement bracket disposed within the housing, wherein the at least one multilayer is secured to the second securement bracket at a position adjacent to the trailing edge, at least one detector disposed adjacent to the trailing edge of the at least one multilayer, wherein the detector is adapted to detect the impingent high-energy photons after interaction with the at least one multilayer, and at least one adjustment mechanism operatively connected to the second securement bracket, wherein the at least one adjustment mechanism adjusts the position of the second securement bracket to alter an angular position of the at least one multilayer;

a first communication link connected to the at least one detector to transmit electrical signals from the at least one detector;

a processor connected to the first communication link to receive the electrical signals from the at least one detector and generate control signals for the at least one adjustment mechanism; and a second communication link connected between the processor and the at least one adjustment mechanism.

13. The detection system of claim 12, further comprising:
a signal conditioning module disposed between the at least one detector and the processor to amplify the electrical signals from the at least one detector before being transmitted to the processor.

14. The detection system of claim 12, wherein the processor is adapted to generate a spectrum associated with the plurality of high-energy photons.

15. A modular detector apparatus for electromagnetic radiation originating from a source, the modular detector apparatus comprising:

a first detector module, the first detector module comprising
a first housing,
at least a first multilayer disposed within the first housing, the first multilayer defining a first leading edge and a first trailing edge, wherein the first multilayer is adapted to interact with a plurality of high-energy photons within the X-ray portion of the electromagnetic spectrum, impingent from the first leading edge, to permit passage of photons of at least one selected from a plurality of different energies,
a first securement bracket disposed within the first housing, wherein the first multilayer is pivotally fixed to the first securement bracket at a position adjacent to the first leading edge,
a second securement bracket disposed within the first housing, wherein the first multilayer is adjustably supported by the second securement bracket at a position adjacent to the first trailing edge,
a first screen disposed adjacent to the first leading edge of the first multilayer, wherein the first screen is adapted to adjust the vertical acceptance of the impingent high-energy photons,
at least a first detector disposed adjacent to the first trailing edge of the first multilayer, wherein the first detector is adapted to detect the impingent high-energy photons after interaction with the first multilayer;

a second detector module, the second detector module comprising
a second housing,
at least a second multilayer disposed within the second housing, the second multilayer defining a second leading edge and a second trailing edge, wherein the second multilayer is adapted to interact with a plurality of high-energy photons within the X-ray portion of the electromagnetic spectrum, impingent from the second leading edge, to permit passage of photons of at least one selected from a plurality of different energies,
a third securement bracket disposed within the second housing, wherein the second multilayer is pivotally fixed to the third securement bracket at a position adjacent to the second leading edge,
a fourth securement bracket disposed within the second housing, wherein the second multilayer is adjustably supported by the fourth securement bracket at a position adjacent to the second trailing edge,
a second screen disposed adjacent to the second leading edge of the second multilayer, wherein the second screen is adapted to adjust the vertical acceptance of the impingent high-energy photons,
at least a second detector disposed adjacent to the fourth trailing edge of the second multilayer, wherein the second detector is adapted to detect the impingent high-energy photons after interaction with the second multilayer;

a screen adjustment mechanism operatively connected to one of the first screen and the second screen;

a screen connector configured to couple the first screen and second screen providing, in cooperation with the screen adjustment mechanism, synchronized movement of the first screen and the second screen;

an adjustment mechanism connected to one of the second securement bracket and the fourth securement bracket; and a ring connector configured to couple the second securement bracket and the fourth securement bracket providing, in cooperation with the adjustment mechanism, synchronized movement of the second securement bracket and the fourth securement bracket allowing adjustment of the position of the second securement bracket and the fourth securement bracket to alter an angular position of the first multilayer and the second multilayer wherein the first multilayer is oriented along a first radial line extending outwardly from the source and second multilayer is oriented along a second radial line extending outwardly from the source.

16. The modular detector apparatus of claim 15 wherein one of the first multilayer and the second multilayer has a body defining a surface with a grading ratio, wherein the grading ratio follows the equation:

$$d/d_0 = R/R_0$$

wherein d is a d-spacing of the multilayer at a distance R from a center point, and wherein $d_0$ is the d-spacing at $R_0$, which is a minimum value for the at least one multilayer.

17. A method for detecting at least a portion of a spectrum of electromagnetic radiation comprising:

positioning at least one detector at a predetermined distance from an electromagnetic radiation source, wherein the electromagnetic radiation source emits at least X-rays and the at least one detector detects at least the X-rays;

positioning at least one graded multilayer between the at least one detector and the electromagnetic radiation source, wherein the at least one graded multilayer interacts with the X-rays to permit X-rays with first predetermined energies to pass to the at least one detector and wherein the at least one multilayer has a body defining a surface with a grading ratio, wherein the grading ratio follows the equation:

$$d/d_0 = R/R_0$$

wherein d is a d-spacing of the multilayer at a distance R from a center point, and wherein $d_0$ is the d-spacing at $R_0$, which is a minimum value for the at least one multilayer;

detecting a first quantity of X-rays with the first predetermined energies by the detector;

adjusting the position of the at least one graded multilayer to permit X-rays with second predetermined energies, different from the first predetermined energies, to pass to the at least one detector; and detecting a second quantity of X-rays with the second predetermined energies by the detector.

18. The method of claim 17, further comprising:

iteratively repeating the adjusting of the position of the at least one graded multilayer and the detecting of a quantity of X-rays until a spectrum spanning a predetermined range of predetermined X-ray energies is collected.

19. The method of claim 17, wherein the detector is at least one selected from a group comprising a proportional counter, a scintillation counter, an ionization chamber, and a solid-state detector.

20. A method for detecting at least a portion of a spectrum of electromagnetic radiation comprising:

positioning at least one detector at a predetermined distance from an electromagnetic radiation source, wherein the electromagnetic radiation source emits at least X-rays and the at least one detector detects at least the X-rays;

positioning at least one graded multilayer between the at least one detector and the electromagnetic radiation source, wherein the at least one graded multilayer interacts with the X-rays to permit X-rays with first predetermined energies to pass to the at least one detector;

mounting a first edge of the at least one graded multilayer on a first radius line;

mounting a second edge of the at least one graded multilayer on a second radius line;

mounting a first edge of at least a second graded multilayer on the first radius line;

mounting a second edge of at least the second graded multilayer on the second radius line;

wherein the first radius line and the second radius line are concentric, with a common center point at the electromagnetic radiation source;

positioning a plurality of adjustable beam entrance slits between the electromagnetic radiation source and the at least one graded multilayer and the second graded multilayer, wherein the plurality of adjustable beam entrance slits are adapted to control the vertical and horizontal acceptance angles relative to the center point;

adjusting an orientation of the at least one graded multilayer and the second graded multilayer to maintain an angular relationship between the multilayers; and wherein adjusting the orientation comprises moving the second edges of the multilayers while maintaining the first edges in a stationary position;

detecting a first quantity of X-rays with the first predetermined energies by the detector;

adjusting the position of the at least one graded multilayer to permit X-rays with second predetermined energies, different from the first predetermined energies, to pass to the at least one detector; and detecting a second quantity of X-rays with the second predetermined energies by the detector.

21. The method of claim 20, further comprising:

iteratively repeating the adjusting of the position of the at least one graded multilayer and the detecting of a quantity of X-rays until a spectrum spanning a predetermined range of predetermined X-ray energies is collected.

22. The method of claim 20, wherein the detector is at least one selected from a group comprising a proportional counter, a scintillation counter, an ionization chamber, and a solid-state detector.

* * * * *